US 6,758,836 B2

United States Patent
Zawacki (10) Patent No.: US 6,758,836 B2
(45) Date of Patent: Jul. 6, 2004

(54) SPLIT TIP DIALYSIS CATHETER

(75) Inventor: John A. Zawacki, Salt Lake City, UT (US)

(73) Assignee: C. R. Bard, Inc., Murray Hill, NJ (US)

(*) Notice: Subject to any disclaimer, the term of this patent is extended or adjusted under 35 U.S.C. 154(b) by 182 days.

(21) Appl. No.: 10/072,788

(22) Filed: Feb. 7, 2002

(65) Prior Publication Data

US 2003/0149395 A1 Aug. 7, 2003

(51) Int. Cl.[7] .................... A61M 25/00; A61M 3/00; A61M 37/00
(52) U.S. Cl. .................... 604/284; 604/6.16; 604/43
(58) Field of Search .................... 604/6.16, 27, 29, 604/30, 33, 35, 39, 40, 43, 48, 93.01, 94.01, 164.01, 164.02, 164.04, 171, 173, 174, 249, 264, 275, 284, 523, 533, 534, 535, 537, 538, 539

(56) References Cited

U.S. PATENT DOCUMENTS

| | | |
|---|---|---|
| 1,696,018 A | 12/1928 | Schellberg |
| 2,393,002 A | 1/1946 | Smith |
| 3,416,532 A | 12/1968 | Grossman |
| 3,426,759 A | 2/1969 | Smith |
| 3,929,126 A | 12/1975 | Corsaut |
| 4,149,535 A | 4/1979 | Volder |
| 4,385,631 A | 5/1983 | Uthmann |
| 4,493,696 A * | 1/1985 | Uldall .................... 604/43 |
| 4,808,155 A | 2/1989 | Mahurkar |
| 4,842,582 A | 6/1989 | Mahurkar |
| 5,106,376 A | 4/1992 | Mononen |
| 5,221,255 A | 6/1993 | Mahurkar et al. |
| 5,221,256 A | 6/1993 | Mahurkar |
| 5,242,398 A | 9/1993 | Knoll et al. |
| 5,342,295 A | 8/1994 | Imran |
| 5,348,536 A | 9/1994 | Young et al. |
| 5,378,230 A | 1/1995 | Mahurkar |
| 5,395,316 A | 3/1995 | Martin |
| 5,405,341 A | 4/1995 | Martin |
| 5,451,233 A | 9/1995 | Yock |
| 5,472,417 A | 12/1995 | Martin et al. |
| 5,505,710 A | 4/1996 | Dorsey, III |
| 5,571,093 A | 11/1996 | Cruz et al. |
| 5,607,462 A | 3/1997 | Imran |
| 5,624,392 A | 4/1997 | Saab |
| 5,665,067 A | 9/1997 | Linder et al. |
| 5,693,030 A | 12/1997 | Lee |
| 5,718,678 A * | 2/1998 | Fleming, III .................... 604/43 |
| 5,718,692 A | 2/1998 | Schon et al. |
| 5,738,649 A | 4/1998 | Macoviak |

(List continued on next page.)

FOREIGN PATENT DOCUMENTS

| | | |
|---|---|---|
| CA | 1 150 122 | 7/1983 |
| EP | 0 495 263 A1 | 7/1992 |
| WO | WO 97/17102 | 5/1997 |
| WO | WO 02/058776 | 8/2002 |
| WO | WO 03/030960 | 4/2003 |
| WO | WO 03/033049 | 4/2003 |

OTHER PUBLICATIONS

Search Report, Mar. 7, 2003.

*Primary Examiner*—Brian L. Casler
*Assistant Examiner*—Mark K Han
(74) *Attorney, Agent, or Firm*—Morrison & Foerster LLP (57) ABSTRACT

A split tip dialysis catheter having an outer tube and an inner tube, the two tubes which can be arranged over at least a portion of their length in a coaxial configuration. The inner tube may be connected to the outer tube at a proximal bifurcation, secured at a distal end of the outer tube or both, but generally the inner tube will remain free to move relative to the outer tube to optimize functionality. In addition, the inner tube can be arranged to be removable from the catheter for replacement thereof.

46 Claims, 11 Drawing Sheets

U.S. PATENT DOCUMENTS

| | | |
|---|---|---|
| 5,776,111 A | 7/1998 | Tesio |
| 5,792,094 A | 8/1998 | Stevens et al. |
| 5,797,869 A | 8/1998 | Martin et al. |
| 5,800,384 A | 9/1998 | Russell |
| 5,800,414 A | 9/1998 | Cazal |
| 5,807,311 A | 9/1998 | Palestrant |
| 5,807,318 A | 9/1998 | St. Goar et al. |
| 5,810,789 A | 9/1998 | Powers et al. |
| 5,814,016 A | 9/1998 | Valley et al. |
| 5,947,953 A | 9/1999 | Ash |
| 5,989,206 A | 11/1999 | Prosl et al. |
| 6,001,079 A | 12/1999 | Pourchez |
| 6,126,631 A | 10/2000 | Loggie |
| 6,156,016 A | 12/2000 | Maginot |
| 6,161,547 A | 12/2000 | Barbut |
| 6,190,349 B1 | 2/2001 | Ash |
| 6,217,527 B1 * | 4/2001 | Selmon et al. ............... 600/585 |
| 6,293,927 B1 | 9/2001 | McGuckin, Jr. |
| 6,443,922 B1 * | 9/2002 | Roberts et al. ............ 604/4.01 |
| 6,638,242 B2 | 10/2003 | Wilson et al. |
| 6,682,519 B1 | 1/2004 | Schon |
| 6,695,832 B2 | 2/2004 | Schon et al. |
| 2002/0087108 A1 | 7/2002 | Maginot et al. |
| 2002/0091362 A1 | 7/2002 | Maginot et al. |
| 2002/0099327 A1 | 7/2002 | Wilson et al. |
| 2003/0088213 A1 | 5/2003 | Schweikert et al. |
| 2003/0153898 A1 | 8/2003 | Schon et al. |
| 2003/0187411 A1 | 10/2003 | Constantz |

* cited by examiner

SPLIT TIP DIALYSIS CATHETER

FIELD OF THE INVENTION

The present invention relates to catheters and more particularly to catheters used for introduction and removal of fluids from a body.

BACKGROUND OF THE INVENTION

Multi-lumen catheters are used for a variety of applications where it is necessary to have two or more separate fluid pathways. One such application for a multi-lumen catheter is for use in hemodialysis. During hemodialysis, a dual-lumen catheter can be employed to simultaneously accommodate opposing blood flow. More specifically, one lumen aspirates blood from a blood vessel of a patient to a dialysis machine where it is processed for the removal of toxins, while the other lumen infuses the purified blood to the patient.

The primary problem in many dialysis catheters is that related to clotting and fibrin sheath formation. Thrombus and fibrin can occlude distal tips of the catheter lumens, resulting in loss of catheter function when such an occlusion prevents blood flow. This typically occurs initially in the arterial lumen used for aspiration of blood from a patient. A secondary problem is that related to the arterial lumen "sucking" against the vessel wall in which it resides. This problem can occur if the arterial lumen ports become fully occluded by the patient's vasculature. When either of the aforementioned problems is observed clinically, the first attempt at salvaging the catheter is to reverse the bloodlines (i.e., to aspirate through the longer lumen, and to infuse through the shorter lumen, contrary to normal blood flow). While such a scenario causes cleaned blood to flow directly toward the lumen that is under vacuum, line reversal in certain catheters can result in inefficient flow (high re-circulation).

Accordingly, an object of the present invention is to provide a dialysis catheter with adequate profile to allow efficient exchange of blood, while preventing problems associated with occlusion. Another object of the present invention is to provide a dialysis catheter with a moveable lumen so that post-placement adjustment is possible. Further objects and advantages of the present invention will become apparent from the ensuing description and drawings.

BRIEF SUMMARY OF THE INVENTION

In accordance with the present invention, a split tip dialysis catheter comprises an outer tube and an inner tube, wherein the two tubes can be arranged over at least a portion of their length in a coaxial configuration. The inner tube may be connected to the outer tube along a proximal segment, secured at the distal end of the outer tube, or both, but generally the inner tube will remain free to move relative to the outer tube to optimize functionality. In addition, the inner tube can be arranged to be removable from the catheter for replacement thereof. The inner and outer tubes can also be configured to have a differing geometry along their length.

What is claimed is a multi-lumen catheter comprising an outer tube comprising a tip portion, a body portion and a port, wherein the body portion comprises a first lumen, and wherein the tip portion comprises a second lumen in fluid communication with the first lumen, and an inner tube disposed within the body portion of the outer tube along at least a portion of its length, comprising a third lumen, wherein the position of a distal end of the inner tube relative to the port is variable.

DETAILED DESCRIPTION OF THE INVENTION

The following detailed description illustrates the invention by way of example, not by way of limitation, the principles of the invention. This description will clearly enable one skilled in the art to make and use the invention, and describes several embodiments, adaptations, variations, alternatives and uses of the invention, including what we presently believe is the best mode of carrying out the invention.

While a referenced use of the split-tip catheter of the present invention is in attaining short or long term vascular access for hemodialysis, apheresis and hemoperfusion treatments via the subclavian or internal jugular veins, other uses are certainly possible. For example, the split tip catheter of the present invention can be utilized in many applications suitable for a multi-lumen catheter, such as administration of intravenous fluids, blood products, drugs, and parenteral nutrition solutions as well as blood withdrawal.

When used for hemodialysis treatments, the catheter is generally inserted via a cut down or percutaneous procedure into one of the large central veins of the body so that the distal tip lies at the junction of the superior vena cava and the right atrium. The catheter is then tunneled subcutaneously to the desired exit site. Thus, when packaged for use by a vascular surgeon, the catheter of the present invention is accompanied by a tunneler, an introducer, a vessel dilator, a guidewire, a needle, adhesive dressings, injection caps (for luer locks) and a heparin label. When packaged for use by an interventional radiologist, the package further includes a second, larger dilator and a microintroducer as well as an additional guidewire. Of course, as mentioned, the above insertion technique and packaging are offered only for example purposes and certainly other insertion techniques and packages would be equally preferred based on the use of the catheter.

Figure 1:
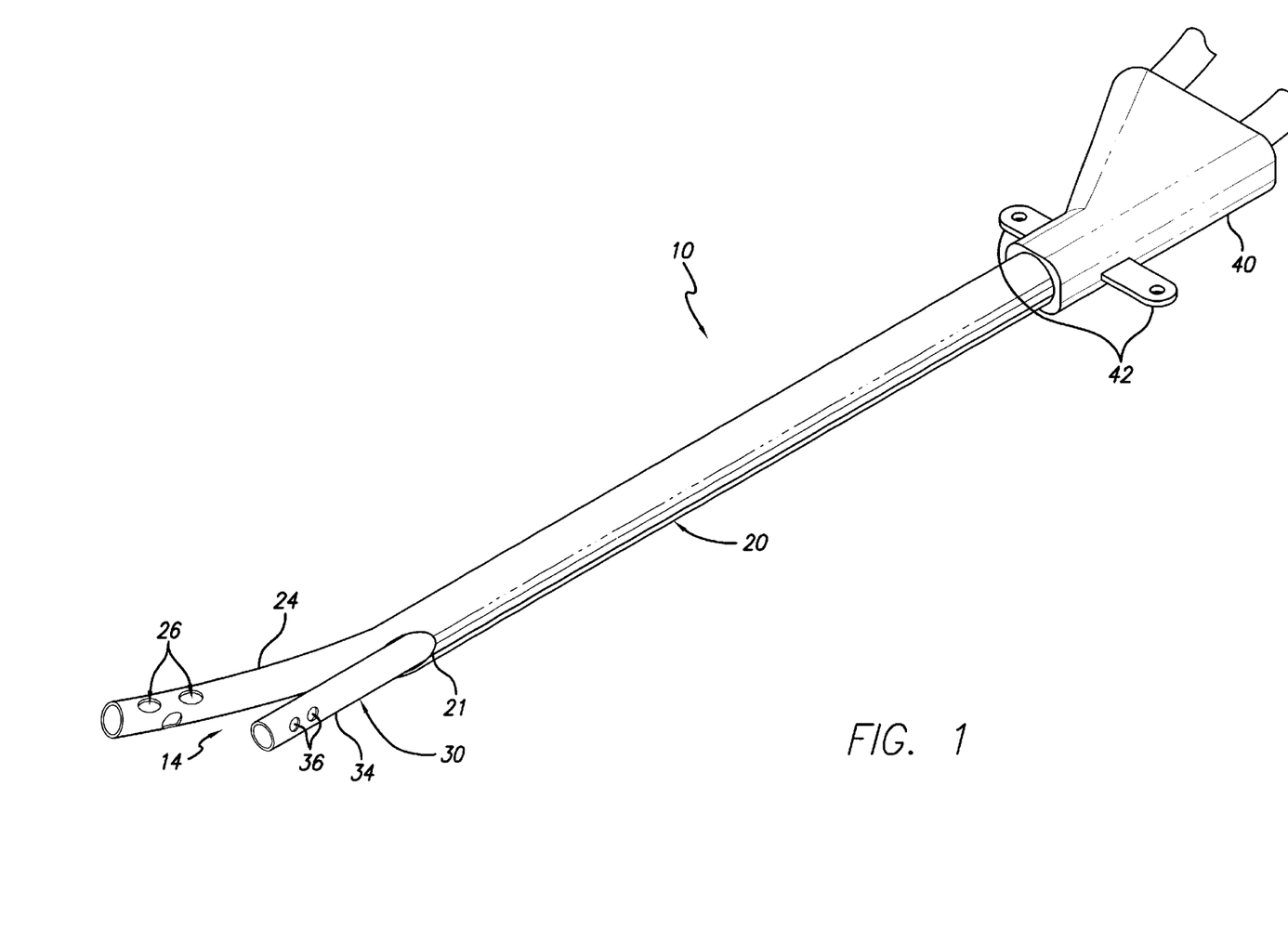
FIG. 1 is a plan view of a preferred embodiment of the split tip catheter of the present invention.

Referring now to FIG. 1, a preferred embodiment of the present invention is shown. Split tip catheter 10 has an inner tube 30 in coaxial relationship to an outer tube 20 along a majority of their length. Each tube 20, 30 is generally comprised of the same type of material if fusing at the proximal end is performed, including thermoplastics such as polyurethane and thermosets such as silicone. Of course, there are many other suitable catheter materials, including, for example, polytetrafluoroethylene and expanded polytetrafluoroethylene.

The outer tube 20 has a proximal portion and a tip portion 24 and is round in cross-section, though many other shapes are certainly possible (for example oval, D-shaped and wedge-shaped). The tip portion 24 is a smaller diameter than the body of the tube 20 and can be formed in a number of ways, such as fusing a primary and secondary tube to one another via radio frequency. By creating the outer tube 20 in this fashion, only a portion of the available lumen area of the primary tube is utilized. The remaining open lumen area of the outer tube 20 allows the passage of the inner tube 30. As can be seen from FIG. 1, at a distal portion 14 of the catheter 10, the inner tube 30 exits the outer tube 20 from a hole or port 21 at the distal end of the outer tube 20.

Figure 2:
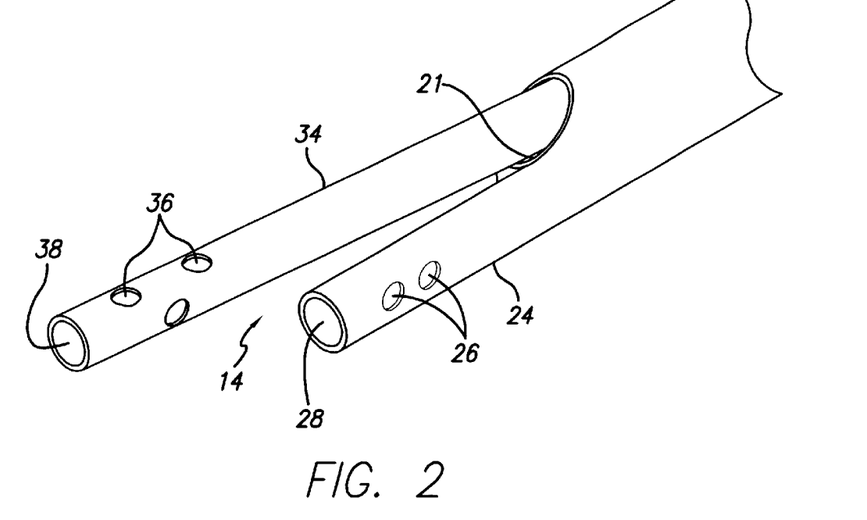
FIG. 2 is a close-up view of the distal portion of the catheter of FIG. 1 in a first position.

Both tip portion 24 of the outer tube 20 and distal end 34 of the inner tube 30 have open ends 28, 38 to allow passage of fluids (see FIG. 2). In addition, holes 26, 36 respectively are arranged around the entire circumference of each portion 24, 34 to facilitate fluid flow and to prevent blockages from occurring. These holes 26, 36 can be arranged in various configurations around the distal tip portions, including staggered or straight line. At a proximal end of the catheter 10, proximal portions of the outer tube 20 and inner tube 30 are coupled together by a hub 40. The hub 40, in addition to arranging the tubes in coaxial alignment with one another, may also have wings 42 for securement of the catheter. Such a hub can be formed in a number of ways, such as insert molding or injection molding over molding rods. In addition to, or in place of the hub 40, the inner tube 30 can be fused to the outer tube 20 at the proximal end of the catheter 10. Of course, a tissue in-growth cuff (not shown) is generally also placed around the outer tube 20 near the proximal end of the catheter 10 to promote tissue in-growth, which aids in securing the catheter 10 in place. The cuff can be fused, solvent bonded or held in place via friction fit.

Figure 3:
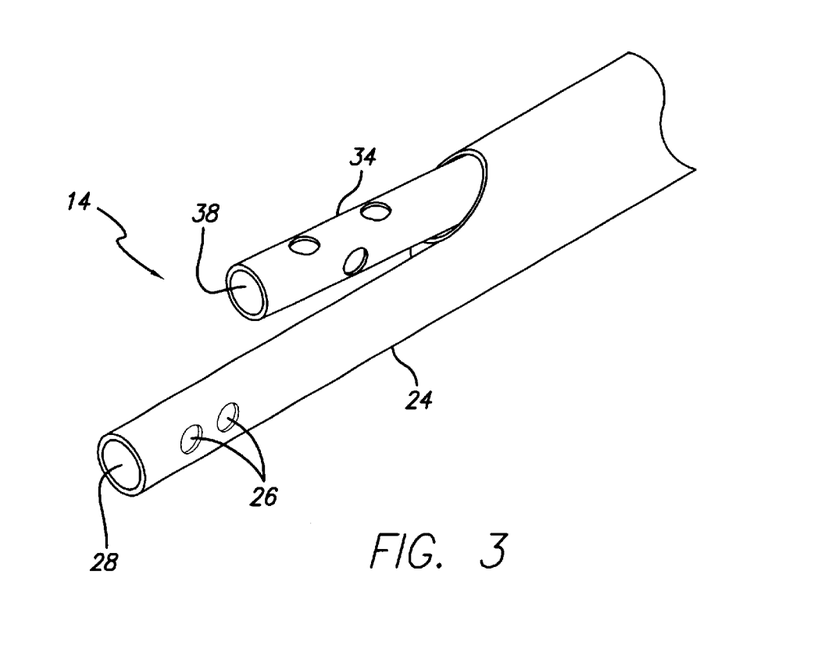
FIG. 3 is a close-up view of the distal portion of the catheter of FIG. 1 in a second position.

Referring now to FIGS. 2 and 3, a close-up view of the distal end 14 of the catheter 10 is shown. FIG. 2 illustrates the positioning of the distal end portion 34 of the inner tube 30 with respect to the tip portion 24 of the outer tube 20 as it would be for normal dialysis treatment. The inner tube 30 is used in this embodiment for infusion of blood through open end 38 and side holes 36, while the outer tube 20 is used for the aspiration of blood through open end 28, side holes 26 and port 21. FIG. 3 shows the positions of the tip portion 24 and the distal end portion 34 reversed so that the inner tube 30 is used for aspiration and the outer tube 20 is used for infusion. This ability to alter the positioning of the distal end 34 of the inner tube 30 in relation to the port 21 and tip portion 24 of the outer tube 20 is extremely useful in cases where line reversal is needed due to blockages, and in particular, the design disclosed herein enables the efficient operation of reverse flow so that an appreciable drop-off in flow efficiency does not occur.

It should be appreciated that many different configurations of the disclosed preferred embodiment are possible, including variations with regard to shape of the tubes, catheter materials and standard catheter features. For example, the distal tip portions of the inner and outer tubes could be shaped differently than the tube body and each other. To increase stiffness, limit radial movement and/or reduce kinking an internal septum for the inner tube, the outer tube or both could be employed (see FIG. 10). In addition, the inner or outer tubes (or both) could have more than one lumen and could be manufactured having different durometers or radiopacifiers to improve physical properties such as reducing kinking, minimizing wall thickness, or radiopacity (different radiopacity could be used, for example, to help a physician distinguish between arterial and venous tips when viewed under x-ray).

In another configuration of a multi-lumen catheter according to the present invention, a reinforcing element could be added to the external wall of one or all of the tubes to increase stiffness and/or reduce kinking. For example, referring to FIG. 1, the outer tube 20 and the inner tube 30 could have a reinforcing element (such as a coil, braid, wire, bead, etc.) wrapped around the walls thereof, embedded or co-extruded. In the case of the inner tube 30, the reinforcing element would have to be low in profile or begin a set distance from the distal end of the inner tube 30 so that movement with respect to the port 21 is not impeded. Of course, the reinforcing element could be applied to other embodiments within the scope of the present invention that are not coaxial in nature as well, such as circle-C, double-D, or shotgun profile configurations.

As shown in FIGS. 1–3, the port 21 through which the inner tube 30 exits the distal end of the outer tube 20 is sized to accommodate the diameter of the distal portion 34 of the inner tube 30. In one embodiment, the port provides a somewhat snug fit around the inner tube 30 to ensure stable positioning. In another embodiment, the port is enlarged, thus permitting the distal portion 34 of the inner tube 30 to float freely, as well as enabling aspiration or infusion of fluids therethrough. The port 21 provides the ability to aspirate or infuse at a juncture that is proximal to the most distal end of the catheter 10. This is a very important feature to eliminate problems that can occur with regard to thrombus formation and clotting on the outer surface of the catheter 10 by enabling the pressure associated with the aspiration or infusion of blood through the port 21 to dislodge any clotting formations on the outer wall of those portions of the catheter 10 distal to the port 21.

Figure 4:
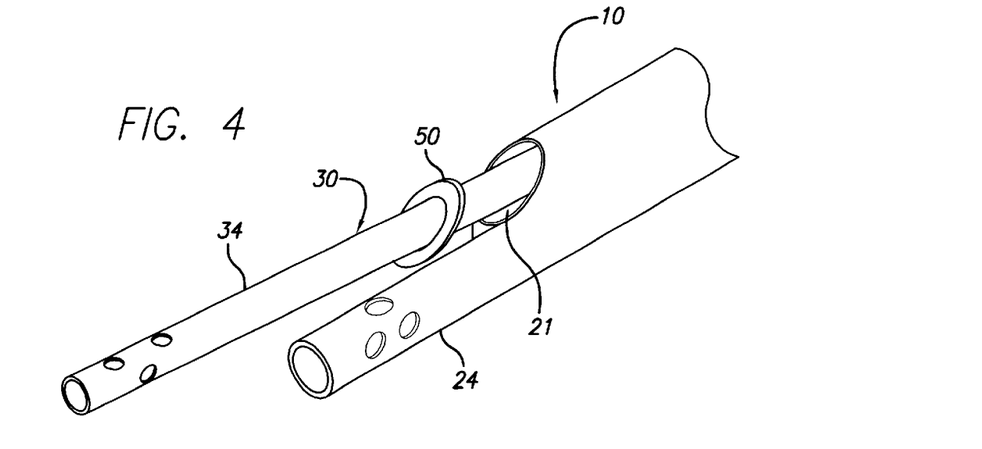
FIG. 4 is a view of an optional configuration of the distal end portion of the catheter of FIG. 1.

FIG. 4 illustrates an optional feature with regard to the port 21, wherein a flap valve 50 is attached to the inner tube 30 to control the flow of blood or fluid, the valve 50 having a similar shape and size as the port 21. The flap valve 50 acts to control the amount of fluid flow through the port 21. For instance, if more aspiration were desired, inner tube 30 with attached flap valve 50 could be distanced from the port 21 to allow blood to be more freely drawn therethrough. On the other hand, to restrict or prevent fluid flow through the port 21, the inner tube 30 could be positioned in varying degrees in close approximation to the port 21 or completely against the port 21. Moreover, the valve 50 can be utilized after periods of dormancy between treatments (when the valve would be closed) to push away thrombus or fibrin prior to initiating dialysis.

Figure 5:
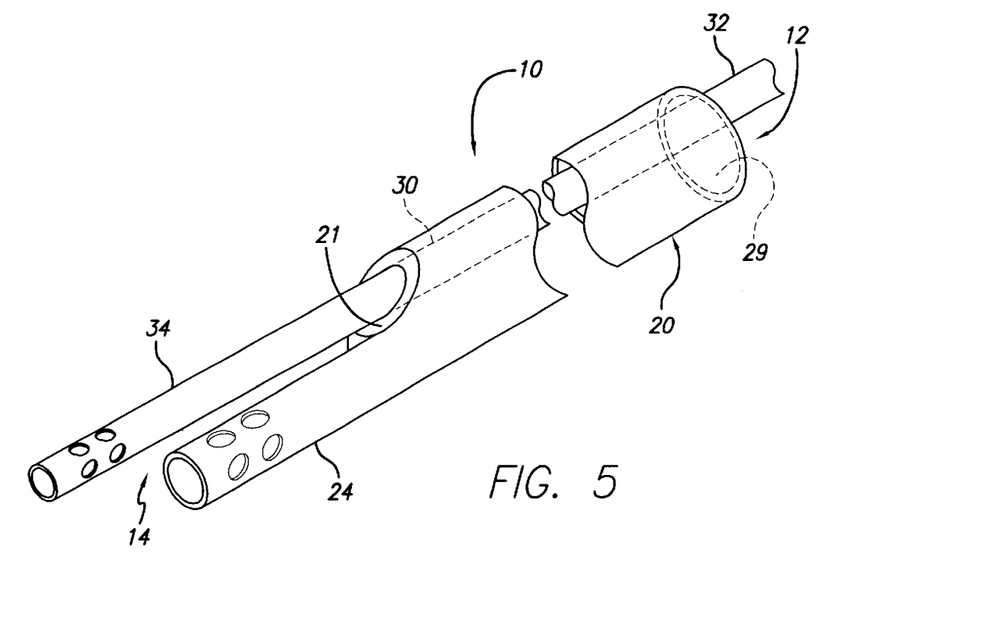
FIG. 5 is view of a catheter according to the present invention, showing both proximal and distal ends.
Figure 6:
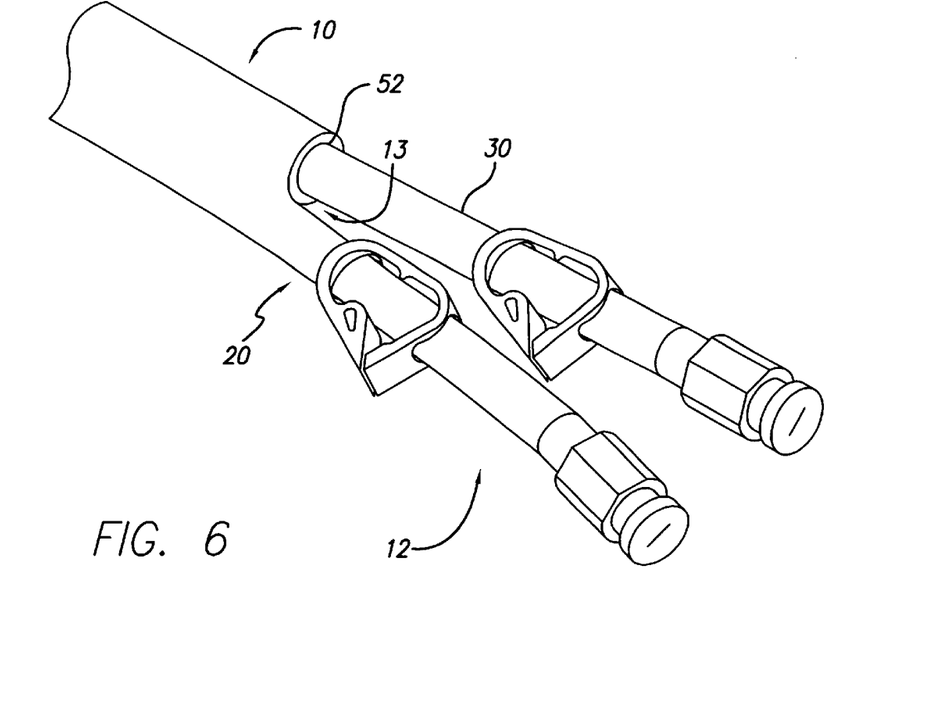
FIG. 6 is a view of a proximal portion of a catheter according to the present invention.

FIG. 5 illustrates a proximal end 12 of the catheter 10 with an optional configuration. As shown, the distal portion 34 of the inner tube 30 is relatively secured by friction fit of the port 21 of outer tube 20. Because of the relative securement at the distal end 14, the inner tube 30 can remain free floating through the open end 29 of the outer tube 20. FIG. 6 illustrates a different configuration for the proximal end 12 of the catheter 10, with the inner tube 30 secured to the outer tube 20 via a releasable seal 52 that would hold the inner tube 30 in place at the bifurcation 13, but would allow movement thereof. Thus, the inner tube 30 could be moved axially in a proximal or distal direction to adjust tip stagger, to actuate an arterial lumen valve (such as the flap valve 50 mentioned in connection with FIG. 4) to seal off flow, or to remove the inner tube 30 altogether for replacement thereof. The seal 52 would also allow rotational movement so that the distal tip 34 of inner tube 30 can be adjusted in the event that side holes 36 become occluded and/or to accommodate optimal side hole positioning to improve flow performance. In addition, rotation of the inner tube 30 may facilitate thrombus removal, thereby increasing the longevity of the catheter 10.

Figure 7:
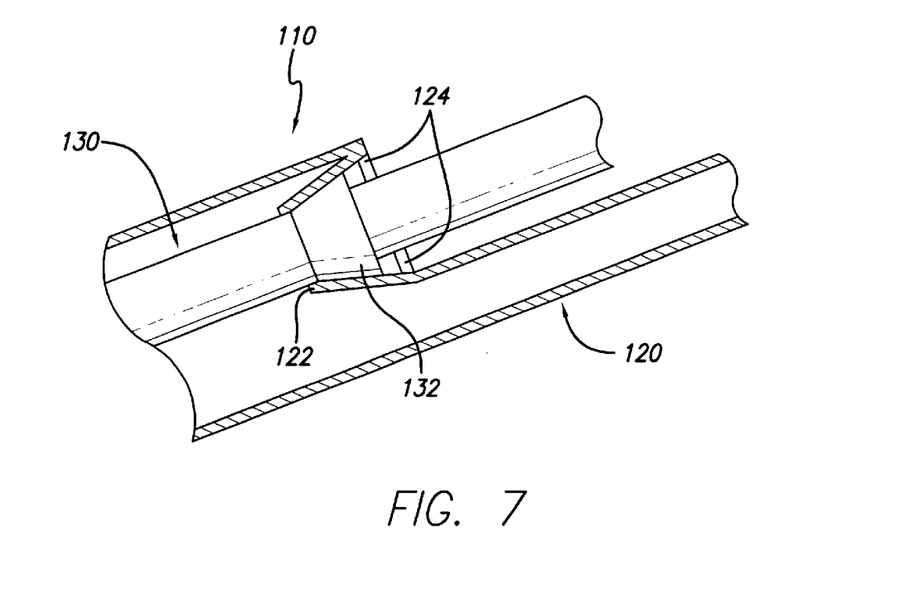
FIG. 7 is a cross-sectional view of a proximal portion of another catheter according to the present invention.

FIG. 7 illustrates an alternate seal for the proximal end portion of the catheter of the present invention. Catheter 110 has an outer tube 120 and an inner tube 130 in a coaxial configuration. Inner tube 130 has a tapered portion 132 such that the largest diameter thereof is greater than the smallest diameter entry point 122 of the outer tube 120 to cause a seal when the tapered portion 132 is disposed therein and to prevent axial movement of the inner tube 130 in a distal direction. The outer tube 120 is also fitted with a set-screw, clip, or pin 124 above entry point 122 and the tapered portion 132 of the inner tube 130 to prevent axial movement in a proximal direction. Thus, a releasable seal is created, where slight axial movement of the inner tube 130 is possible for circumferential rotation of the inner tube 130. The tapered portion 132 could be a collar overmolded onto the inner tube 130 or alternatively could simply be a flared portion thereof. Of course, any type of fastener could be used in connection with, or in place of, pin 124 for preventing axial movement of the catheter 110 in a proximal direction. Most preferably, however, the fastener would be difficult for the patient to manipulate or remove so that accidental removal of the inner tube 130 could not take place. Safety precautions to achieve this objective could include a special tool to be used with the fastener so that only a medical professional could remove the inner tube 130, if desired.

Figure 7A:
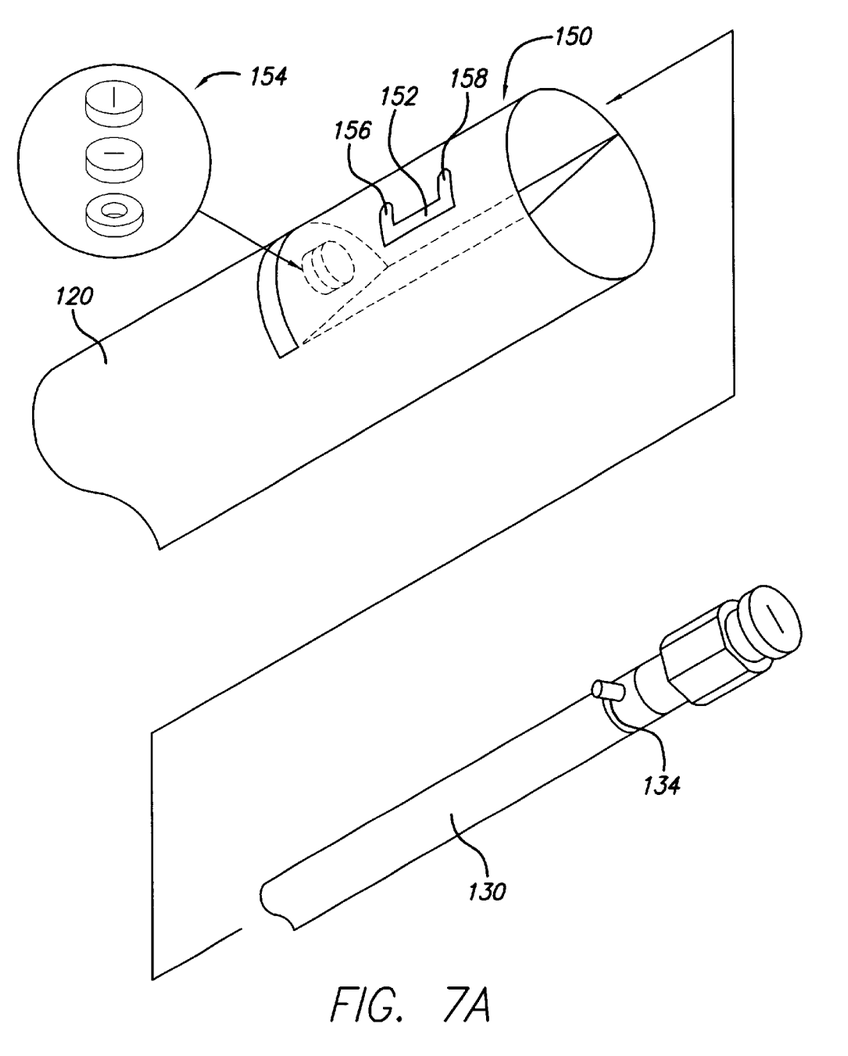
FIG. 7A is a view of a catheter according to the present invention, showing the proximal portion of an outer and an inner tube.

Referring now to FIG. 7A, another embodiment akin to the releasable seal of FIG. 7 is illustrated. In this embodiment, a chamber 150 is located in the proximal end of the outer tube 120. At the base of the chamber, a seal valve 154 is positioned to regulate the flow of fluid and enables the removal of the inner tube 130 in the event of complete occlusion or other malfunctioning. The seal valve 154 depicted is a three-piece device consisting of two disks with slits perpendicular to one another and a third disk with a hole through its center. Of course other possibilities with regard to valve structure is certainly possible to achieve the goals of the present invention. A side wall of the chamber 150 has a guide track 152 for receiving a pin 134, which is incorporated into the inner tube 130 (for example, by molding thereon). The guide track 152 permits axial movement of the inner tube 134 over a set distance, such that the inner tube 130 can be locked at a distal distance and a proximal distance when the pin 134 engages a recess at each end of the guide track 152. Thus, for example, the length of the guide track 152 could be fashioned such that locking points 156, 158 are provided at the distal and proximal end respectively of the guide track 152. When the pin 134 is positioned within the distal locking point 156, the tip of the inner tube 130 is distal to the tip of the outer tube 120. Conversely, when the pin 134 is positioned within the proximal locking point 158, the tip of the inner tube 130 is proximal to the tip of the outer tube 120. Such a design would enable the tips to be reversed so that the normally longer venous lumen (inner tube 130) could become the arterial lumen for purposes of reversing the lines.

Figure 7B:
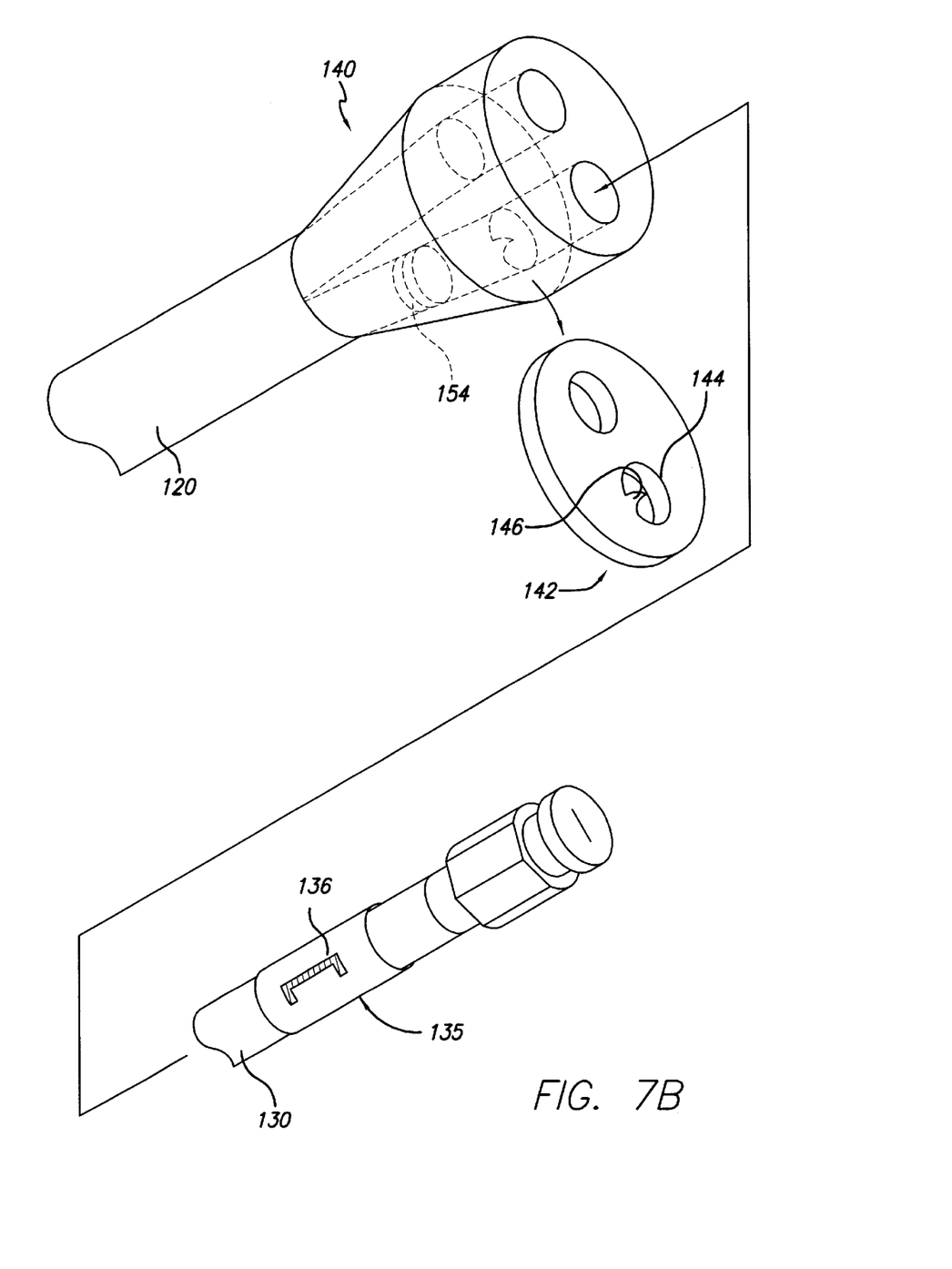
FIG. 7B is a view of another catheter according to the present invention, showing the proximal portion of an outer and an inner tube.

A similar embodiment to that shown in FIG. 7A is illustrated in FIG. 7B. In this embodiment, a guide track 136 is incorporated into the inner tube 130 rather than into the outer tube 120. This can be accomplished by creating the guide track 136 with material routed out of a collar 135 as shown, or alternatively by molding additional material into the collar 135 (such that a ridge-like configuration would be produced). The outer tube 120 is shown with a bifurcation 140, having the seal valve 154 through which inner tube 130 is placed and a plate 142 for receiving the inner tube with guide track 136. The plate 142 has a opening 144 for the tube 130, the opening 144 having a pin 146 to mate with the guide track 136. As with the embodiment shown in FIG. 7A, the pin 146 and guide track 136 are constructed so that a set distance is permitted for travel by the inner tube 130, providing two locking points which position the inner tube 130 distal to and proximal to the tip of the outer tube 120. Of course, if the guide track is a ridge-like configuration, the pin 146 will be shaped differently to accommodate movement and locking of the position of the inner tube 130.

Figure 7C:
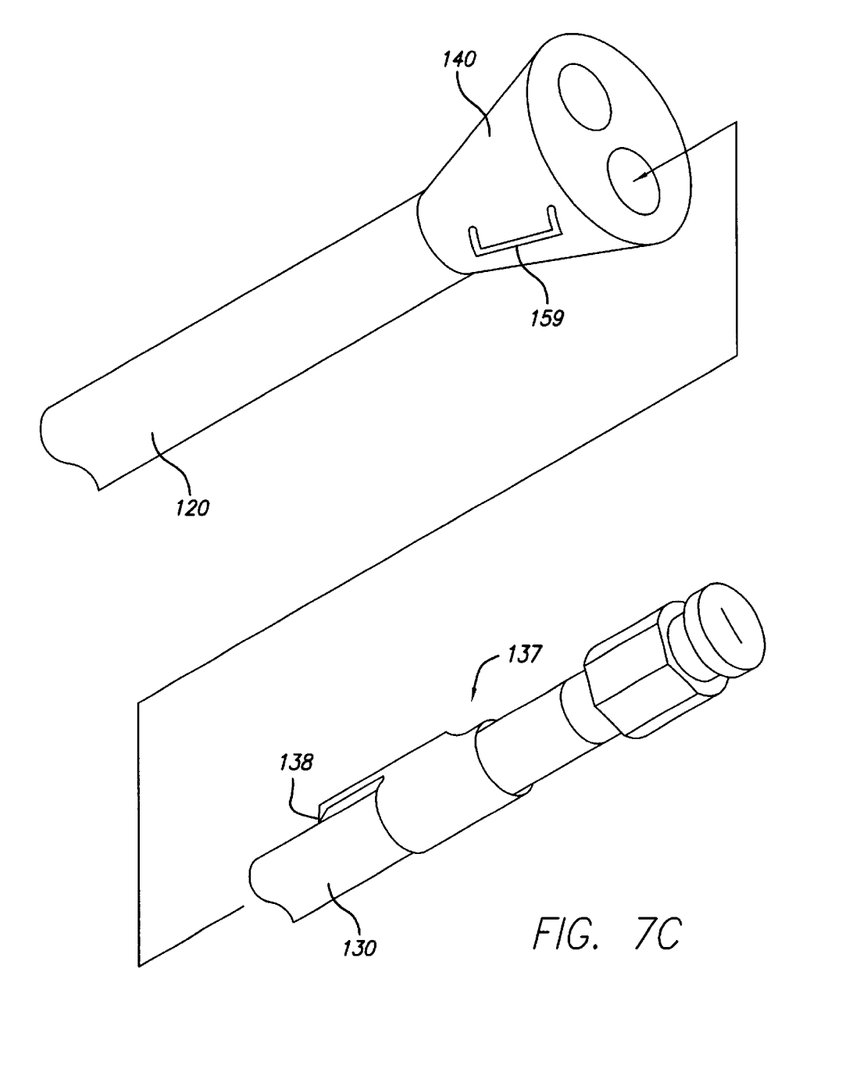
FIG. 7C is a view of yet another catheter according to the present invention, showing the proximal portion of an outer and an inner tube.

FIG. 7C illustrates yet another embodiment along the same lines of FIGS. 7A and 7B. In this embodiment, a guide track 159 is incorporated into the outer surface of the bifurcation 140. A collar 137 having a pin 138 is fitted or molded to the outer surface of the inner tube 130. Thus, when the inner tube 130 is placed within the bifurcation for passage through the outer tube 120, the pin 138 is positioned within the guide track 159 to limit the axial movement of the inner tube 130 with respect to the outer tube 120. As with the above embodiments, a fixed distance can be set so that locking points at each end of the guide track 159 position the tip of the inner tube 130 distal to and proximal to the tip of the outer tube 120 when the pin 138 is placed therein. It should be appreciated, however, that different configurations for the guide track are possible, including different lengths, locking points and positioning within the system.

Figure 7D:
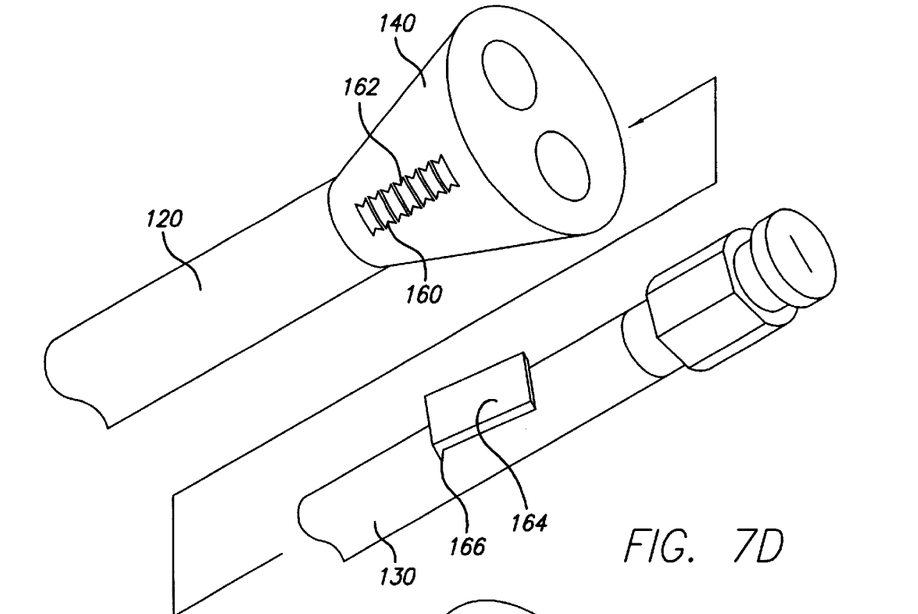
FIG. 7D is a view of still another catheter according to the present invention, showing the proximal portion of an outer and an inner tube.
Figure 7E:
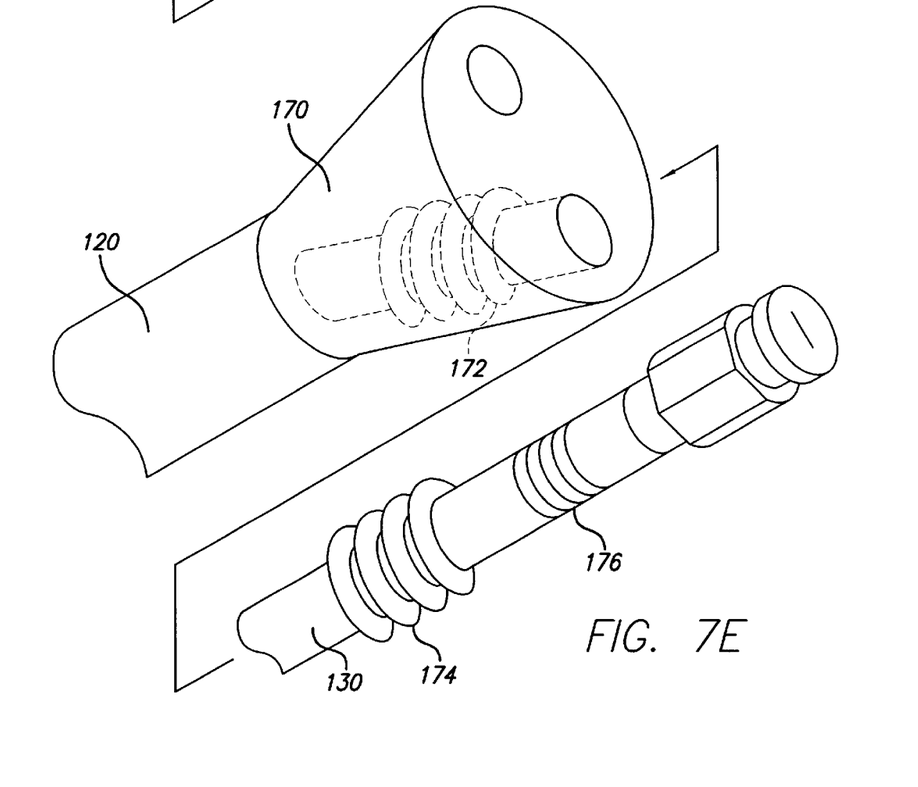
FIG. 7E is a view of another catheter according to the present invention, showing the proximal portion of an outer and an inner tube.

FIGS. 7D and 7E illustrate two further embodiments of the present invention similar to those mentioned above. In FIG. 7D, a guide track 160 is incorporated into the outer surface of the bifurcation 140, having teeth 162. A thumb slide 164 with a engaging point 166 is molded or fit onto the outer surface of the inner tube 130 for receipt thereof by the teeth 162. This design affords even more control over the axial positioning of the inner tube 130 with respect to the outer tube 120 as the inner tube 130 will be locked into place at several points along the length of the guide track 160. Precise positioning can be ensured through design of the teeth. For instance, if very small increments were desirable, the teeth 162 and the engaging point 166 could be made quite tiny. On the other hand, larger teeth 162 and engaging point 166 could be fashioned for larger desired increments.

FIG. 7E shows inner tube 130 with overmolded threads 174 incorporated on the outer surface thereof. These threads 174 are designed to mate with tapped threads 172 in a bifurcation 170. The distance of the distal ends of the inner tube 130 with respect to the outer tube 120 can be controlled and monitored through use of depth markings 176 on the outer surface of the inner tube 130 proximal to the overmolded threads 174. Of course, a reverse-type embodiment is also possible with the male threaded portion being within the bifurcation 170 and the female threaded portion being incorporated into the inner tube 130. Also, with respect to the depth markings, all of the embodiments above would certainly benefit from such markings and, indeed, it is contemplated by the present invention that each embodiment have a similar tracking and monitoring system of axial placement associated therewith.

The design of the releasable seal in FIG. 7 and the other embodiments in FIGS. 7A–E, relating to fixed axial movement of the inner tube with respect to the outer tube removes a design constraint for using materials that will fuse together. Thus, in connection with these embodiments, dissimilar materials could be used for the outer and inner tubes 120, 130 such as thermoplastics (e.g. polyurethane) and thermosets (e.g. silicone). For example, the inner tube 130 could be made of polyurethane while the outer tube 120 could be made of silicone to take advantage of the strength, thin walls and stiffness characteristics of polyurethane and the chemical compatibility and kink resistance characteristics of silicone. Also, materials with the same classification but with substantially different melting temperatures could be utilized for each of the outer and inner tubes 120, 130. Further, because the outer and inner tubes 120, 130 are not fused together, the inner tube 120 can readily be replaced in the case of a failure or occlusion that leads to less than optimal performance. The replacement of the inner tube 120, as mentioned above, preferably will require a special tool or method to free the inner tube 120 from any locking mechanism or fastener holding it in place (examples of which can be seen in the foregoing figures), so that accidental removal by a patient does not take place.

Figure 8:
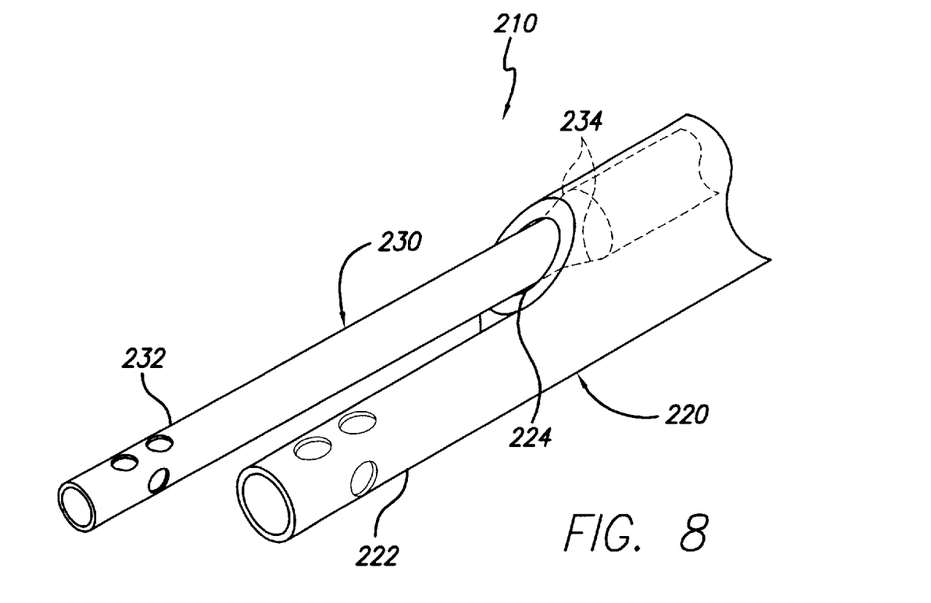
FIG. 8 is a view of a distal end portion of a catheter according to the present invention.

Referring now to FIG. 8, an alternate embodiment of the present invention is shown for the distal portion of the catheter. Catheter 210 has inner tube 230 disposed coaxially within outer tube 220, the tubes 230, 220 having distal tip portions 232, 222 respectively. In this embodiment, the inner tube 230 is characterized by a tapered portion 234, which resides within the outer tube 220 proximal to a port 224. The tapered portion 234 serves a dual purpose of providing a releasable seal to partially or completely block fluids from entering the port 224 and for permitting the inner tube 230 to extend a predetermined distance from the port 224.

Figure 9:
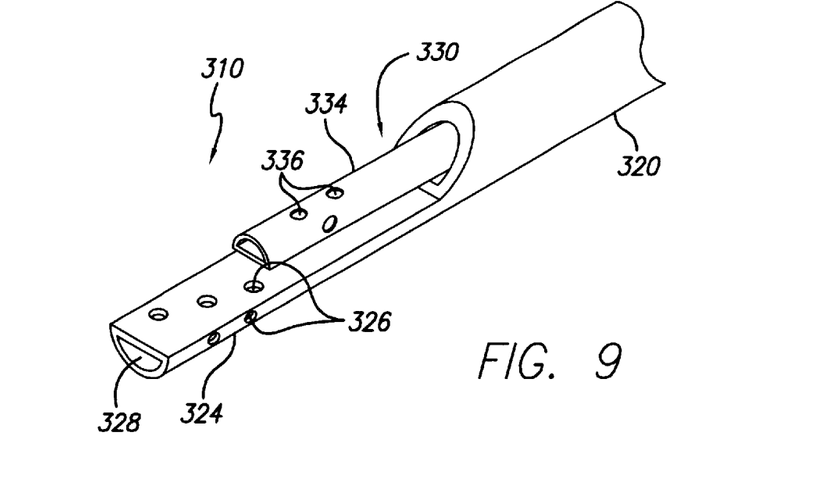
FIG. 9 is a view a distal end portion of a catheter according to the present invention, showing an alternate configuration thereof.

FIG. 9 shows an alternate embodiment of the catheter of the present invention with respect to the geometry of the tubes. Catheter 310 has an outer tube 320 and an inner tube 330, each having distal portions 324, 334 respectively. The distal portions 324, 334 are D-shaped so that the flat portions of each are directly opposing one another. This reduces the profile of the catheter 310 to facilitate introduction to the blood vessel of a patient. While not shown, it is certainly conceivable that only the distal portion 334 of the inner tube 330 has a D-shaped profile, while the remainder of the body is circular in cross-section or some other shape which would enhance physical characteristics of the catheter 330. In addition, the cross-section of the outer tube could vary along its length to promote beneficial characteristics of the catheter 320, depending on its location in the body (see FIG. 14, below).

Figure 10:
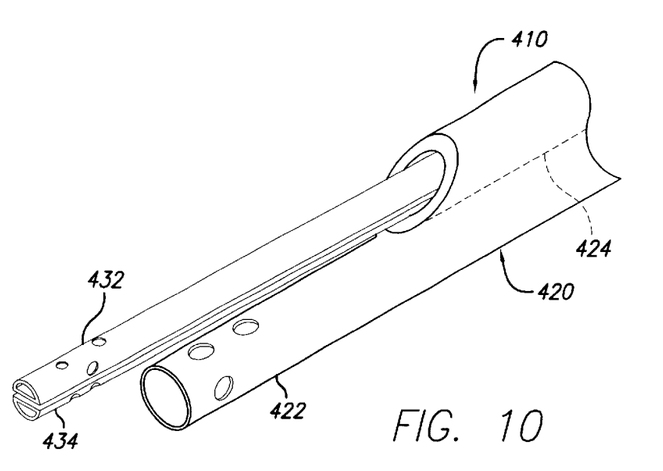
FIG. 10 is a view of the distal end of a catheter of the present invention showing a dual inner lumen configuration for an inner tube thereof.

FIG. 10 illustrates a further embodiment of the present invention, with the inner tube comprising two tubes 432, 434 at least at the distal end of the catheter 410. A single inner tube could be divided into the two tubes 432, 434 at some point along the length of the catheter 410 or the two tubes could be separate along their entire length. As with the other examples provided herein, the geometry of the catheters can also vary along their length to optimize their physical characteristics. As shown, the tubes 432, 434 have a D-shape configuration with the flat portions opposing one another to reduce their collective profile. The distal portion 422 of the outer tube 420 is shown as circular in cross-section, though certainly many other possibilities exist, such as oval, D-shaped, trapezoidal, triangular and wedge-shaped, to name a few.

Figure 11:
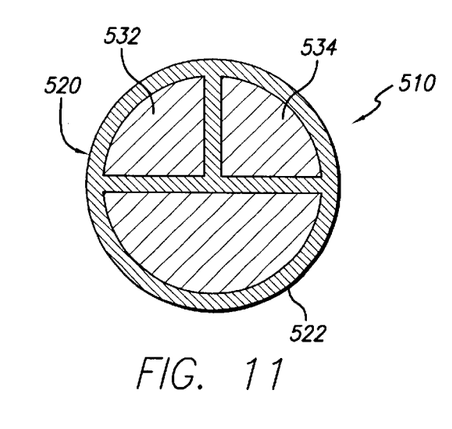
FIG. 11 is a cross-sectional view of an alternate dual inner lumen configuration according to the present invention.
Figure 12:
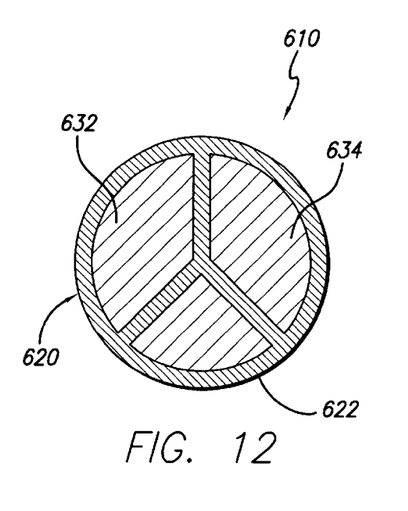
FIG. 12 is a cross-sectional view of another dual inner lumen according to the present invention.

FIGS. 11 and 12 illustrate from an cross-sectional view of the catheter a few of the aforementioned possibilities. In FIG. 11, a catheter 510 is shown with an outer catheter 520 having a D-shaped distal portion 522. The inner tube, as with FIG. 10, consists of two separate tubes 532, 524 at least at the distal portion of the tube, the tubes 532, 534 having a divided D-shape configuration. This geometry maximizes the available area of the inner tube 520 at the distal end, matching with the distal portion 522 to complete in combination the circular proximal cross-section of the inner tube 520. In FIG. 12, a catheter 610 is shown with an outer catheter 620 having a wedge-shaped distal portion 622. The inner tube, as with FIGS. 10 and 11, is made up of two separate tubes 632, 634 at least at the distal portion of the tube. Again, as with the configuration in FIG. 11, the circular proximal cross-section of the outer tube 620 is maximized at the distal end by having the inner tubes 632, 624 having similar wedge-shaped configurations as the distal portion 622 of the outer tube 620, where the combination of the three tubes approximately covers the surface area of a circle.

Figure 13:
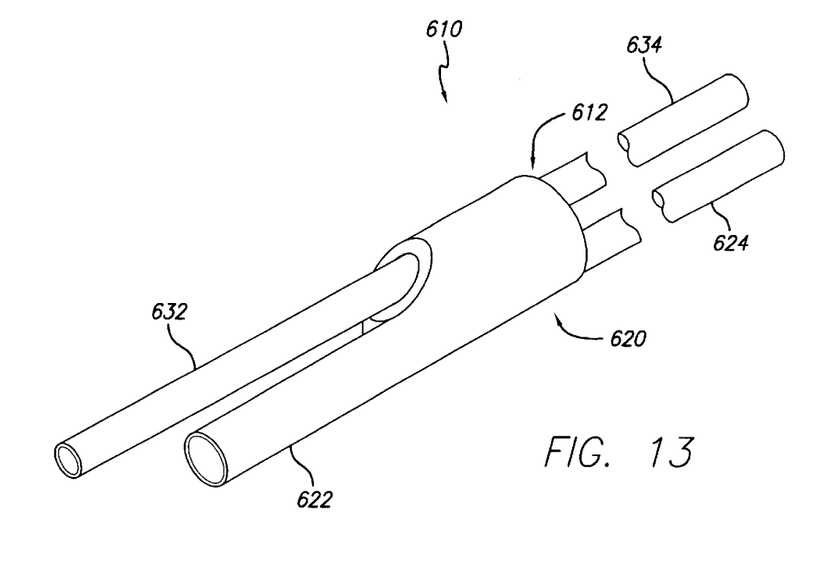
FIG. 13 is a view of a profile transition for a catheter according to the present invention.

Referring back to FIG. 10. a septum 424 is shown within the outer tube 420, which will act to increase stiffness, limit radial movement and/or reduce kinking of the outer tube 420. Of course, as mentioned above, a septum could also be placed within the inner tubes 432, 434 and/or the outer distal portion 422 to also take advantage of the stated benefits. While the examples thus far have shown the inner and outer tubes in a coaxial relationship with the inner tube within the outer tube along a majority of their length, other embodiments are possible in the spirit of the present invention. For instance, instead of having a coaxial configuration from the bifurcation to the distal tips, differing tube profiles may be joined using a transition at some point along the catheter. FIG. 13 shows one possibility in this regard, with catheter 610 having dual proximal tubes 624, 634, which transition to a coaxial configuration at transition point 612 with an inner tube 632 inside of an outer tube 620 having distal portion 622. In this design, as with others mentioned herein, differing tube profiles are also possible, one example being a transition from a coaxial, to a double-D configuration.

Figure 14:
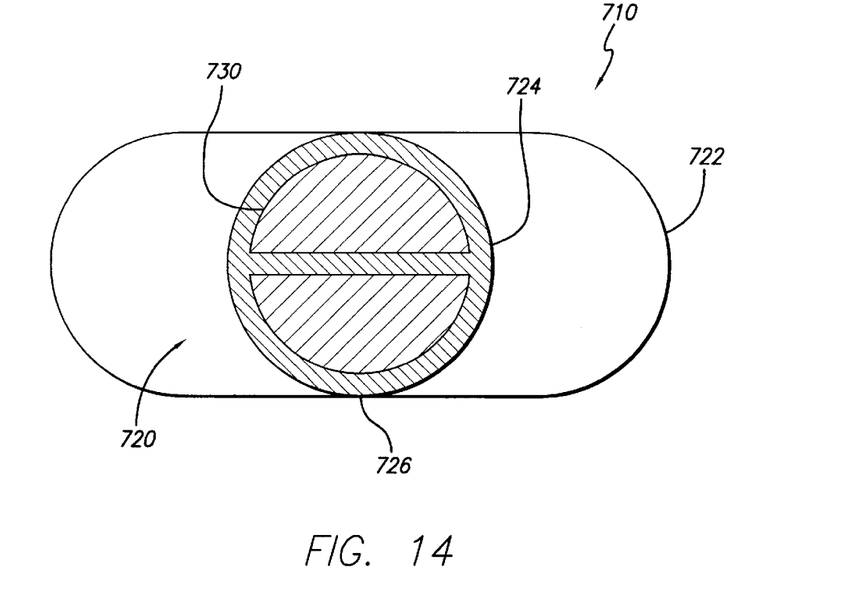
FIG. 14 is an cross-sectional view of another profile transition for a catheter according to the present invention.

FIG. 14 shows another transition embodiment from cross-sectional view. A catheter 710 has an outer tube 720, which transitions from an oval-shaped proximal portion 722 to a circular distal portion 724 at a transition point. The two portions 722, 724 can be attached at the transition point through methods known in the art, such as via fusion by radio frequency or extrusion. The distal portion 724 terminates in a D-shaped distal tube 726, matching an inner tube distal portion 730, which is also D-shaped to maximize the area of the circular cross-section of distal portion 724, similarly to that shown in FIG. 9. The oval-shaped profile of the proximal portion 722 is optimal for kink resistance, but takes up more space within the blood vessel in which the catheter 710 is placed. The transition point is envisioned as being located near the venotomy site. The distal portion 724 is smaller in profile and therefore is able to travel within the blood vessel. Thus, several goals are achieved through transitioning of profiles in this fashion, including at least the maximization of kink resistance, and the minimization of surface area for the portion of the catheter inserted within the blood vessels. It should also be appreciated that more than one transition is possible along the length of the outer tube, the inner tube or both, and certainly a number of transitions could be utilized to maximize the physical attributes and functionality of the catheter as a whole.

The present invention has been described above in terms of a presently preferred embodiment so that an understanding of the present invention can be conveyed. However, there are many alternative arrangements for a split-tip catheter not specifically described herein but with which the present invention is applicable. Although specific cross-sectional shapes and lengthwise configurations have been given, the catheter of the present invention would equally be embodied by other shapes and sizes not specifically recited herein. The scope of the present invention should therefore not be limited by the embodiments illustrated, but rather it should be understood that the present invention has wide applicability with respect to split-tip catheters generally. All modifications, variations, or equivalent elements and implementations that are within the scope of the appended claims should therefore be considered within the scope of the invention.

I claim:

1. A multi-lumen catheter, comprising:
    an outer tube comprising a tip portion, a body portion and a port, wherein the body portion comprises a first lumen, and wherein the tip portion comprises a second lumen in fluid communication with the first lumen; and
    an inner tube disposed within the body portion of the outer tube along at least a portion of its length, comprising a third lumen, wherein the position of a distal end of the inner tube relative to the port is variable;
    wherein the outer tube further comprises a releasable seal at the proximal end thereof, wherein the inner tube is secured by the releasable seal.

2. The multi-lumen catheter according to claim 1, wherein the tip portion is smaller in diameter than the body portion.

3. The multi-lumen catheter according to claim 1, wherein the tip portion further comprises at least one opening.

4. The multi-lumen catheter according to claim 1, wherein the tip portion further comprises a plurality of side holes spaced around the circumference thereof.

5. The multi-lumen catheter according to claim 1, wherein the distal end of the inner tube comprises at least one opening.

6. The multi-lumen catheter according to claim 1, wherein the distal end of the inner tube comprises a plurality of side holes spaced around the circumference thereof.

7. The multi-lumen catheter according to claim 1, wherein said outer tube is comprised of a material selected from the group consisting of polyurethane, silicone, polytetrafluoroethylene and expanded polytetrafluoroethylene.

8. The multi-lumen catheter according to claim 1, wherein said inner tube is comprised of a material selected from the group consisting of polyurethane, silicone, polytetrafluoroethylene and expanded polytetrafluoroethylene.

9. The multi-lumen catheter according to claim 1, wherein said outer and inner tubes are comprised from the same material.

10. The multi-lumen catheter according to claim 1, wherein said outer and inner tubes are comprised from a different material.

11. The multi-lumen catheter according to claim 1, wherein the cross-sectional shape of the body portion of the outer tube is selected from the group consisting of circular, oval, trapezoidal, D-shaped and wedge-shaped.

12. The multi-lumen catheter according to claim 1, wherein the cross-sectional shape of the tip portion of the outer tube is selected from the group consisting of circular, oval, trapezoidal, D-shaped and wedge-shaped.

13. The multi-lumen catheter according to claim 1, wherein the cross-sectional shape of the inner tube is selected from the group consisting of circular, oval, trapezoidal, D-shaped and wedge-shaped.

14. The multi-lumen catheter according to claim 1, further comprising a radiopaque portion.

15. The multi-lumen catheter according to claim 1, wherein the body portion of the outer tube further comprises a reinforcing element.

16. The multi-lumen catheter according to claim 1, wherein the inner tube further comprises a reinforcing element.

17. The multi-lumen catheter according to claim 1, wherein the inner tube is fused to the outer tube at a proximal end thereof.

18. A multi-lumen catheter, comprising:
    an outer tube comprising a tip portion, a body portion and a port, wherein the body portion comprises a first lumen, wherein the tip portion comprises a second lumen in fluid communication with the first lumen, and wherein the body portion further comprises a septum; and
    an inner tube disposed within the body portion of the outer tube along at least a portion of its length, comprising a third lumen, wherein the position of a distal end of the inner tube relative to the port is variable.

19. A multi-lumen catheter, comprising:
    an outer tube comprising a tip portion, a body portion and a port, wherein the body portion comprises a first lumen, wherein the tip portion comprises a second lumen in fluid communication with the first lumen, and wherein the tip portion further comprises a septum; and
    an inner tube disposed within the body portion of the outer tube along at least a portion of its length, comprising a third lumen, wherein the position of a distal end of the inner tube relative to the port is variable.

20. A multi-lumen catheter, comprising:
    an outer tube comprising a tip portion, a body portion and a port, wherein the body portion comprises a first lumen, and wherein the tip portion comprises a second lumen in fluid communication with the first lumen; and
    an inner tube disposed within the body portion of the outer tube along at least a portion of its length, comprising a third lumen, wherein the position of a distal end of the inner tube relative to the port is variable, and wherein the inner tube further comprises a septum.

21. A multi-lumen catheter, comprising:
    an outer tube comprising a tip portion, a body portion and a port, wherein the body portion comprises a first lumen, wherein the tip portion comprises a second lumen in fluid communication with the first lumen, and wherein the port comprises a valve mechanism to control the flow of fluid therethrough; and an inner tube disposed within the body portion of the outer tube along at least a portion of its length, comprising a third lumen, wherein the position of a distal end of the inner tube relative to the port is variable.

22. A multi-lumen catheter, comprising:

an outer tube comprising a tip portion, a body portion and a port, wherein the body portion comprises a first lumen, and wherein the tip portion comprises a second lumen in fluid communication with the first lumen; and an inner tube disposed within the body portion of the outer tube along at least a portion of its length, comprising a third lumen, wherein the position of a distal end of the inner tube relative to the port is variable;

wherein at least one of the tip portion of the outer tube and the inner tube further comprise a valve mechanism that controls the flow of fluid therethrough.

23. A multi-lumen catheter, comprising:

an outer tube comprising a tip portion, a body portion and a port, wherein the body portion comprises a first lumen, and wherein the tip portion comprises a second lumen in fluid communication with the first lumen; and an inner tube disposed within the body portion of the outer tube along at least a portion of its length, comprising a third lumen, wherein the position of a distal end of the inner tube relative to the port is variable, wherein the inner tube further comprises a tapered portion at the distal end thereof, wherein the diameter of the inner tube proximal to the tapered portion is greater than the diameter of the port.

24. A multi-lumen catheter, comprising:

an outer tube comprising a tip portion, a body portion and a port, wherein the body portion comprises a first lumen, and wherein the tip portion comprises a second lumen in fluid communication with the first lumen;

an inner tube disposed within the body portion of the outer tube along at least a portion of its length, comprising a third lumen, wherein the position of a distal end of the inner tube relative to the port is variable; and a second inner tube, comprising a fourth lumen and at least one opening therein, the fourth lumen being in fluid communication with said at least one opening, wherein the position of a distal end of the second inner tube relative to the port is variable.

25. The multi-lumen catheter according to claim 22, wherein the cross-sectional shape of the inner tube and the second inner tube are substantially similar.

26. The multi-lumen catheter according to claim 22, wherein the cross-sectional shape of at least one of the inner tube and the second inner tube is selected from the group consisting of circular, oval, trapezoidal, D-shaped and wedge-shaped.

27. A multi-lumen catheter, comprising:

an outer tube comprising a tip portion, a body portion and a port, wherein the body portion comprises a first lumen, and wherein the tip portion comprises a second lumen in fluid communication with the first lumen, wherein the body portion further comprises a proximal portion having a first cross-sectional shape and a distal portion having a second cross-sectional shape, wherein the first and second cross-sectional shapes are different from one another; and an inner tube disposed within the body portion of the outer tube along at least a portion of its length, comprising a third lumen, wherein the position of a distal end of the inner tube relative to the port is variable.

28. The multi-lumen catheter according to claim 27 wherein the first and second cross-sectional shapes are joined together at a transition point.

29. A multi-lumen catheter, comprising:

an outer tube comprising a tip portion, a body portion and a port, wherein the body portion comprises a first lumen, and wherein the tip portion comprises a second lumen in fluid communication with the first lumen; and an inner tube disposed within the body portion of the outer tube along at least a portion of its length, comprising a third lumen, wherein the position of a distal end of the inner tube relative to the port is variable, wherein the inner tube further comprises a proximal portion having a first cross-sectional shape and a distal portion having a second cross-sectional shape, wherein the first and second cross-sectional shapes are different from one another.

30. The multi-lumen catheter according to claim 29, wherein the first and second cross-sectional shapes are joined together at a transition point.

31. A multi-lumen catheter, comprising:

an outer tube comprising a tip portion, a body portion and a port, wherein the body portion comprises a first lumen, and wherein the tip portion comprises a second lumen in fluid communication with the first lumen; and an inner tube disposed within the body portion of the outer tube along at least a portion of its length, comprising a third lumen, wherein the position of a distal end of the inner tube relative to the port is variable;

wherein the inner tube further comprises a pin element and the outer tube further comprises a guide track, wherein the pin element is received within the guide track to control the movement of the inner tube with respect to the outer tube.

32. The multi-lumen catheter according to claim 31, further comprising a gauging element to ascertain the position of the inner tube with respect to the outer tube.

33. The multi-lumen catheter according to claim 26, wherein the gauging element is a series of markings disposed on an outer surface of the inner tube.

34. A multi-lumen catheters, comprising:

an outer tube comprising a tip portion, a body portion and a port, wherein the body portion comprises a first lumen, and wherein the tip portion comprises a second lumen in fluid communication with the first lumen;

an inner tube disposed within the body portion of the outer tube along at least a portion of its length, comprising a third lumen, wherein the position of a distal end of the inner tube relative to the port is variable; and a bifurcation element having a first movement control element, wherein the inner tube further comprises a second movement control element, wherein the first and second movement control elements operate together to control the movement of the inner tube with respect to the outer tube.

35. The multi-lumen catheter according to claim 34 wherein the first movement control element is a plate having an opening therein and the second control element is a guide track, and wherein the opening is configured to receive the guide track.

36. The multi-lumen catheter according to claim 35, wherein the opening has a pin element that engages the guide track.

37. The multi-lumen catheter according to claim 34, wherein the first movement control element is a guide track and the second control element is a pin element.

38. The multi-lumen catheter according to claim 37, wherein the guide track is disposed on an inner surface of the bifurcation element.

39. The multi-lumen catheter according to claim 37, wherein the guide track is disposed on an outer surface of the bifurcation element.

40. The multi-lumen catheter according to claim 39, wherein the guide track comprises a set of teeth, and wherein the pin element comprises a thumb slide.

41. The multi-lumen catheter according to claim 34, wherein the first movement control element is a female thread and the second control element is a male thread.

42. The multi-lumen catheter according to claim 23, further comprising a gauging element to ascertain the position of the inner tube with respect to the outer tube.

43. The multi-lumen catheter according to claim 42, wherein the gauging element a series of markings disposed on an outer surface of the inner tube.

44. A multi-lumen catheter, comprising:
   an aspirating tube comprising a tip portion, a body portion and a port, wherein both the tip portion and the body portion have a lumen that together define an arterial lumen; and
   an infusion tube disposed within the body portion of the aspirating tube along at least a portion of its length, comprising a venous lumen, wherein the position of a distal end of the infusion tube relative to the port is variable;
   wherein the aspirating tube further comprises a releasable seal at the proximal end thereof, wherein the infusion tube is secured by the releasable seal.

45. A multi-lumen catheter, comprising:
   an infusion tube comprising a tip portion, a body portion and a port, wherein both the tip portion and the body portion have a lumen that together define a venous lumen; and
   an aspiration tube disposed within the body portion of the infusion tube along at least a portion of its length, comprising an arterial lumen, wherein the position of a distal end of the aspiration tube relative to the port is variable;
   wherein the infusion tube further comprises a releasable seal at the proximal end thereof, wherein the aspiration tube is secured by the releasable seal.

46. A catheter having at least two separate lumens, comprising:
   a first tube comprising a first lumen; and
   a second tube comprising a tip portion, a body portion and a port, wherein both the tip portion and the body portion have a lumen that together define a second lumen, wherein the port is positioned proximal to both the tip portion and a distal end of the first tube, and wherein the port is adapted for the passage of fluid therethrough;
   wherein the second tube further comprises a releasable seal at the proximal end thereof, wherein the first tube is secured by the releasable seal.

* * * * *